United States Patent
Somerson et al.

[11] Patent Number: 6,119,686
[45] Date of Patent: Sep. 19, 2000

[54] APNEA DETECTION FOR MEDICAL VENTILATOR

[75] Inventors: Steven K. Somerson, Madison; Kevin G. Tissot, Brooklyn; Ronald L. Tobia, Sun Prairie, all of Wis.

[73] Assignee: Datex-Ohmeda, Inc., Tewksbury, Mass.

[21] Appl. No.: 08/972,099

[22] Filed: Nov. 17, 1997

Related U.S. Application Data

[63] Continuation of application No. 08/622,901, Mar. 29, 1996, abandoned.

[51] Int. Cl.$^7$ .................................................. A61M 16/00
[52] U.S. Cl. ............................... 128/202.22; 128/204.23; 128/204.21
[58] Field of Search ........................ 128/204.18, 204.21, 128/204.23, 202.22, 205.23

[56] References Cited

U.S. PATENT DOCUMENTS

| | | | |
|---|---|---|---|
| 3,856,051 | 12/1974 | Bain | 128/204.18 |
| 3,961,627 | 6/1976 | Ernst et al. | 128/204.21 |
| 3,972,327 | 8/1976 | Ernst et al. | 128/204.21 |
| 5,315,989 | 5/1994 | Tobia | 128/204.28 |
| 5,390,666 | 2/1995 | Kimm et al. | 128/204.26 |
| 5,522,383 | 6/1996 | Sullivan et al. | 128/204.26 |
| 5,540,220 | 7/1996 | Gropper et al. | 128/204.26 |
| 5,603,316 | 2/1997 | Coufal et al. | 128/204.23 |
| 5,626,129 | 5/1997 | Klimm et al. | 128/202.22 |
| 5,794,614 | 8/1998 | Gruenke et al. | 128/204.21 |
| 5,832,916 | 11/1998 | Lundberg | 128/202.22 |
| 5,860,418 | 1/1999 | Lundberg | 128/202.22 |
| 5,865,171 | 2/1999 | Cinquin | 128/203.12 |
| 5,881,717 | 3/1999 | Isaza | 128/202.22 |

*Primary Examiner*—Aaron J. Lewis
*Attorney, Agent, or Firm*—Andrus, Sceales, Starke & Sawall

[57] ABSTRACT

An apnea detection system is disclosed for use with a medical ventilator and which detects the volume of gas delivered by the ventilator to a patient and also the volume of gas exhaled by the patient. The two flow measurements are compared, preferably in a microprocessor, to determine whether an apnea condition exists by comparing, against a known standard, the two detected volumes. The volume of the exhaled gas must be a predetermined percentage of the volume of gas delivered to the patient within a predetermined time period or an alarm is activated indicating an apnea condition.

17 Claims, 3 Drawing Sheets

APNEA DETECTION FOR MEDICAL VENTILATOR

This is a continuation of application Ser. No. 08/622,901 filed Mar. 29, 1996, now abandoned.

BACKGROUND OF THE INVENTION

This invention relates to medical ventilators and, more particularly, to an improved system for detecting an apnea condition in the delivery system for a medical ventilator.

In general, medical ventilator systems are used to provide respiratory support and anesthesia to patients undergoing medical treatment. The primary function of the ventilator is to maintain suitable pressure and flow of gases inspired and expired by the patient. Ventilator systems which are used in the administration of anesthesia to a patient undergoing an operation may include a bellows arrangement through which anesthetic gasses are provided to the patient. Alternatively, when used in ICU settings, the ventilator may provide flow directly to the patient.

The gasses actually delivered to the patient normally travel through a patient circuit that is generally a disposable unit having one end coupled to the patient via a face mask or other administration device and the other end is connected to the ventilator or to a bellows. According to the preference of the user, there are several differing types of patient circuits which can be used to deliver gasses to the patient. Perhaps the most common patient circuit is the standard circle system where there are separate limbs for providing the inhalation gas to a patient from the ventilator and for receiving the exhaled gases from the patient. Alternatively there may be a Bain circuit which again is commonly used and comprises one tubing enclosed within another or a modified Bain/Mapleson patient circuit where, again, there are coaxial tubes.

Among the normal monitoring functions of medical ventilators is the apnea alarm, that is, the alarm that signals to the user that breathing has ceased or has been reduced to an unacceptable level. Current apnea alarms are generally based on the volume of gas exhaled from the patient and therefore monitor the flow during the patient's exhalation through the use of a flow sensor. That flow is then integrated with respect to time to obtain a determination of exhalation volume and the apnea alarm signals if that exhaled volume is not of a predetermined value within a predetermined time period, indicating that the patient is not properly exhaling. As such, therefore, the conventional system uses a single flow sensor in the patient circuit at or near the patient in the expiratory limb of the patient circuit.

One of the difficulties with the use of a single flow sensor is that in the case of some circuit disconnects, i.e. a loss of pneumatic integrity of the ventilator system, it is possible to still see flow through the expiratory flow sensor, thus the apnea alarm will not always be triggered in a situation where an apnea condition exists. For example, there could be a partial patient disconnect that could be a problem in ventilating the patient, yet, if the threshold value that the flow sensor must see is relatively low, the flow sensor may see sufficient flow exhaled by the patient so that the apnea alarm would not be activated. Increasing the threshold value to correct this problem would negate the alarms efficacy when ventilating with small volumes.

Accordingly, the reliance on a single flow sensor that is positioned to sense the exhalation of the patient may not be sufficient to properly identify and signal an apnea condition that has taken place in the ventilator system.

SUMMARY OF THE INVENTION

There is thus provided an improved system for the detection and alarming of an apnea condition in a ventilator system providing ventilation to a patient. In the present system, both the inspiratory and the expiratory volumes of gas in the patient circuit are monitored which provides better and more sensitive recognition of apnea. In some circuits two flow sensors are employed and in other circuits only one flow sensor is utilized, however in either case, a flow sensor means detects both the inhalation flow and the exhalation flow to and from the patient. The flow sensing means provides a signal indicative of such flow to a CPU to integrate the signal with respect to time in order to provide a determination of the volume that is administered to the patient and the volume of gas that is exhaled by the patient.

By monitoring the inspiratory and the expiratory volume to and from the patient, a relationship can be determined as to the proportionate value of those volumes on which to detect and alarm for an apnea condition. For example, depending on the type of patient circuit, a relationship can be used to determine the expected percentage of the volume of exhalation gas volume as compared to the inhalation volume delivered and, if that exhalation volume percentage is not recognized within a predetermined period of time, an alarm is activated indicating the presence of an apnea condition.

In addition, since the present invention may be used with a variety of patient breathing circuits, the specific circuit utilized can be inputted to the CPU so that the desired proportion can be used in determining an apnea condition for that particular circuit. That input may be manually inputted by the user or the system may have an automatic recognition system that identifies the patient circuit being used and input that information to the CPU without intervention of the user.

While the preferred form of the invention is described as using a ventilator, it will be understood that the apnea alarm system could be equally applicable where the ventilator is not actually providing mechanical ventilation to the patient, that is, where the clinician may be manually bagging the patient or the patient is carrying out spontaneous breathing.

Other objects, features and advantages of the present invention will be more readily apparent from the detailed description of the preferred embodiment set forth below, taken in conjunction with the accompanying drawings.

DESCRIPTION OF THE PREFERRED EMBODIMENT

Figure 1:
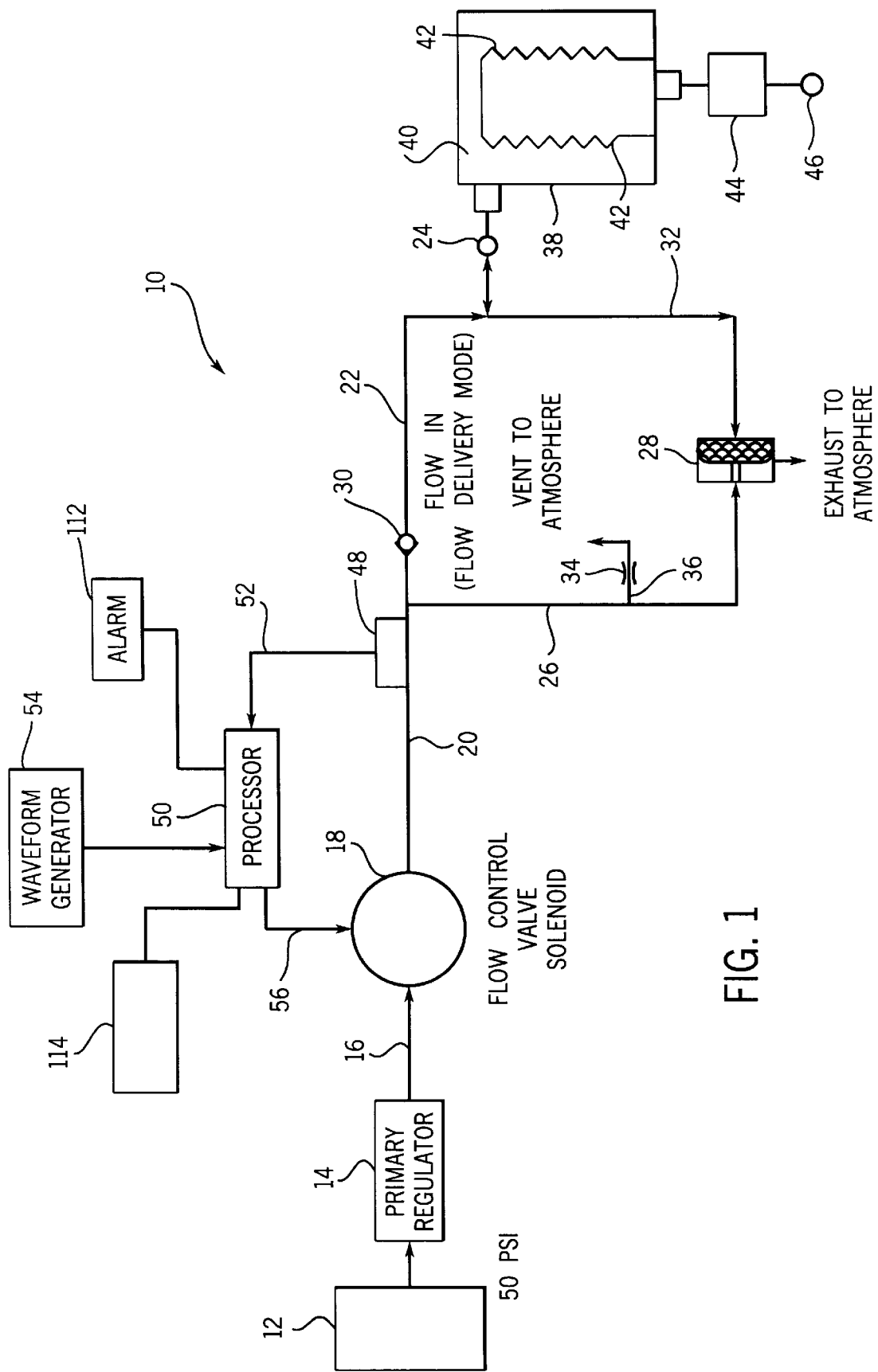
FIG. 1 is a block diagram of the overall ventilator system that may be used with the present invention.

Referring now to FIG. 1, there is shown a schematic view of a ventilator apparatus suitable for carrying out the present invention. The mechanical aspects of the ventilator apparatus are similar to those disclosed in U.S. Pat. No. 5,315,989 of Tobia and the disclosure of which is incorporated herein by reference, however, there are some differences in the systems and such differences will become apparent from the following description.

Ventilator 10 comprises a gas source 12 which typically provides gas at about 50 psi through a primary regulator 14 to source conduit 16 and which thus supplies flow control valve 18 with gas at approximately 26 psi. Flow control valve 18 is preferably a proportional solenoid valve and which controls the magnitude of gas flow into conduit 20. Conduit 22 communicates with conduit 20 and provides an inspiratory flow branch to ventilator connection 24. An expiratory flow branch is provided by expiratory conduit 32 which functions to convey gas from ventilator connection 24 to expiratory valve 28. Check valve 30 is located in conduit 22 to prevent flow from conduit 22 and expiratory conduit 32 into conduit 20 during expiration of gas from ventilator connection 24.

Expiratory valve 28 controls the pressure and flow through expiratory conduit 32. Expiratory valve 28 is preferably a diaphragm or balloon type of valve which is capable of controlling the pressure in expiratory conduit 32 according to a reference pressure. Reference control pressure is provided to expiratory valve 28 via the pressure control conduit 26. A flow restrictor 34 is provided on vent conduit 36 to provide a bleed for the pressure control conduit 26. When gas pressure in expiratory conduit 32 exceeds the reference pressure in conduit 26, gas is exhausted from expiratory conduit 32 through expiratory valve 28 to the atmosphere. Thus, the pressure in expiratory conduit 32 is controlled by the reference pressure in pressure control conduit 26 which, in turn, is controlled by the flow control valve 18.

Ventilator connection 24 is made to a bellows assembly 38 and conduit 22 communicates with the bellows outer chamber 40 to actuate bellows 42. The patient breathing circuit 44 is in communication with the interior of the bellows 42 and thus is isolated from the gas in the ventilator 10.

As shown, a patient 46 is fluidly connected to the patient breathing circuit 44 and may be connected to the patient breathing circuit 44 by a face mask or other device to administer the gas to the patient 46 and to receive the exhalation therefrom. As will be seen, there are various patient breathing circuits 44 that can and are used with anesthesia systems and the present invention is adaptable for use with any of the circuits herein described or with other circuits that may be used.

Pressure sensor 48 communicates with the interior of conduit 20 and provides a signal indicative of the pressure within conduit 20 to processor 50 via a signal line 52. The pressure in conduit 20 is indicative of the pressure within the bellows outer chamber 40 exterior of the bellows 42. Processor 50 includes a microprocessor connected via an electronic bus to read only memory (ROM) and random access memory (RAM) in a known digital computer configuration.

Waveform generator 54 provides a desired waveform to processor 50. Flow control valve 18 is controlled by the processor 50 via a control signal line 56 to track the desired pressure waveform established by the user.

Conduits 20, 22 and expiratory conduit 32 thus define a ventilator circuit which communicates with the ventilator connection 24. During most of the inspiratory phase of a patient breath, the ventilator 10 operates in the flow delivery mode whereby flow is delivered from gas source 12 through the flow control valve 18 to conduits 20 and 22 and finally to the ventilator connection 24. During most of the expiratory phase of the patient breath, check valve 30 prevents flow from conduit 22 into conduit 20 and gas flows via expiratory conduit 32 to expiratory valve 28 where it is exhausted to the atmosphere. The ventilator thus operates in a flow exhaust mode.

Turning now to FIG. 2A–2C and 3A–3C, there is shown three schematic views setting forth variations of patient breathing circuits 44 that are commonly used in anesthesia and showing specifically the positioning of the flow sensor means used in carrying out the present invention.

Figure 2A:
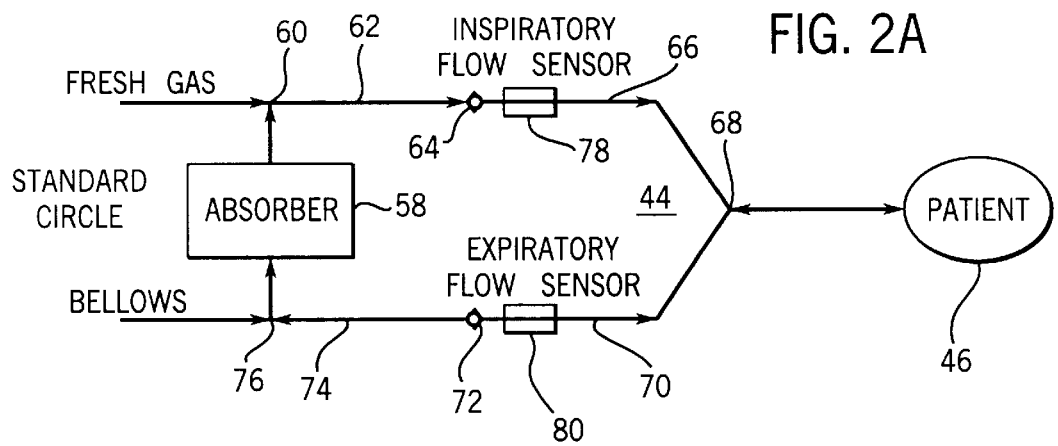
FIGS. 2A–C are schematic views of various patient circuits usable with the present invention and showing the location of the flow sensing means used with the present invention.

In FIG. 2A, the patient breathing circuit 44 is the standard circle system where the gas is received from the bellows 42 (FIG. 1) where that gas passes through an absorber 58 to scrub out $CO_2$ that is built up from the patient's exhalation. The gas from the absorber is mixed with a fresh gas at a tee 60 and the mixture then passes through conduit 62 and a check valve 64 to insure that the flow within the patient breathing circuit 44 is in the proper direction.

Downstream of the check valve 64, the flow enters the inspiratory limb 66 of the patient breathing circuit 44 and then is administered to the patient 46 via a wye piece 68. On the exhalation side of the patient breathing circuit 44, the exhaled gasses from the patient 46 pass through the expiratory limb 70 of the patent circuit 44 and again through a check valve 72 to enter conduit 74 and meet the gas from bellows 42 at tee 76. Thus the gasses then recirculate in a circle configuration.

As also can be seen in FIG. 2A, a flow sensor 78 is located in the inspiratory limb 66 of the patient breathing circuit 44 which senses the flow of gas through that limb and which is inhaled by the patient. A further flow sensor 80 is provided in the expiratory limb 70 to sense the flow in that limb and resulting from the exhalation of the patient 46. Accordingly, a flow sensing means senses both the flow of the gasses to the patient and the flow of gasses from the patient. In both cases, the signals from the flow sensors 78,80 representative of flow in the inspiratory and expiratory limbs 66 and 70, respectively, are transmitted by a suitable electrical bus, not shown, to the processor 50 (FIG. 1) where the flow data is integrated with respect to time to determine the volumetric values of the gas administered to and received from the patient 46.

Figure 3A:
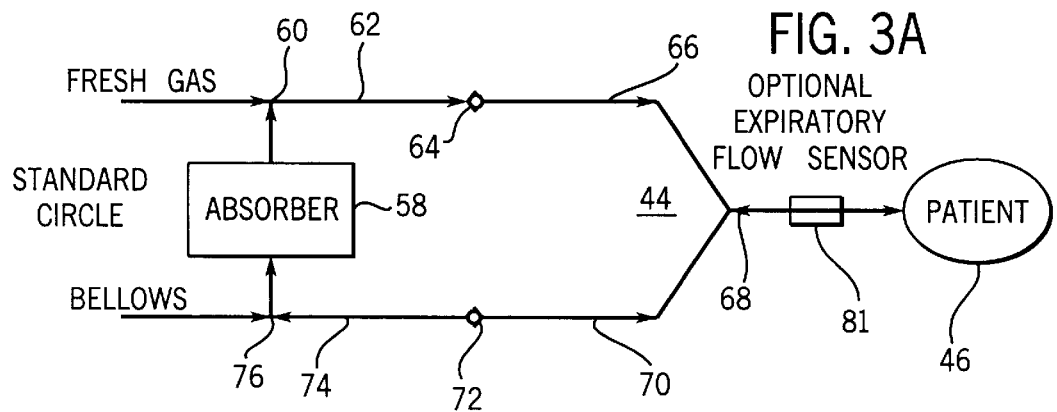
FIGS. 3A–C are schematic views of the various patient circuits of FIGS. 2A–C but having a flow sensing means in an alternate position.

As also can be noted in FIG. 3A, an optional flow sensor 81 may be positioned in the patient breathing circuit 44 as shown in FIG. 2A and is located between the wye piece 68 and the patient 46. In that position, the optional flow sensor 81 senses both the inspiratory flow and the expiratory flow and can transmit the signals representative of those flows to the processor 50 (FIG. 1). Thus, instead of having separate flow sensors in the inspiratory limb 66 and the expiratory limb 70, a single optional flow sensor 81 located toward the patient 46 with respect to the wye piece 68 can sense flow both to and from the patient 46 in that bidirectional flow stream.

Figure 2B:
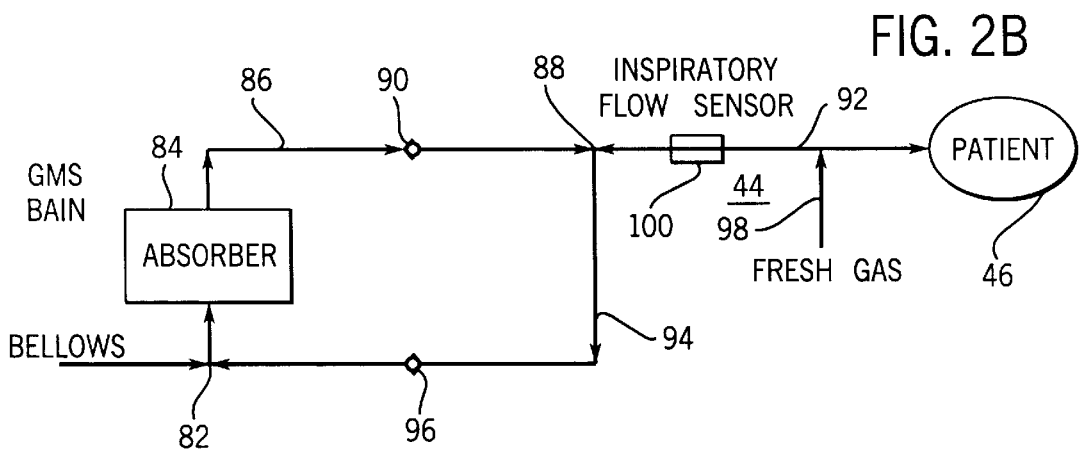

Turning to the FIG. 2B patient circuit, there is shown a schematic view of a Bain type of patient breathing circuit 44 wherein the flow from the bellows 42 enters a tee 82 where the flow continues through the absorber 84 and into conduit 86 to another tee 88. A check valve 90 is provided in the conduit 86 to maintain the flow in the proper direction. The disposable patient breathing circuit 44 is connected to the tee 88 and is basically a flow limb 92 to and from the patient 46.

On the return flow from the patient 46, the flow reverses in the flow limb 92 so that the patient's exhalation returns through the flow limb 92 and, at tee 88, enters conduit 94 where it returns to tee 82 for recirculation. Again, a check valve 96 is provided in the conduit to maintain the overall flow through the system in the proper direction. In this system, the fresh gas in introduced into the patient circuit 44 by means of fresh gas inlet 98.

A flow sensor 100 is provided in the flow limb 92 and determines the bidirectional flow in that limb 92. Therefore, as the flow to administer a breath to the patient 46 is forced by the ventilator, that flow is sensed by the flow sensor 100 and, correspondingly, as the patient exhales, that return flow through the flow limb 92 is again sensed by the flow sensor 100. Accordingly the same flow sensor 100 senses the flow delivered to the patient 46 from the ventilator 10 as well as the flow exhaled by the patient 46.

It should be noted that with this circuit, the flow sensed by the flow sensor 100 in the direction of the patient 46 is the flow from the ventilator 10 and is not the total flow that the patient 46 inhales since additional flow is introduced into the system at the fresh gas inlet 98. Accordingly, additional gas flow is provided to the patient 46 as inhalation and is delivered to the system downstream of the flow sensor 100.

As described previously, the signals from the flow sensor 100 are transmitted by an appropriate bus to the processor 50 where those signals are integrated with respect to time to produce a signal indicative of the volume of gas delivered to the patient circuit 44 from the bellows 42 and that exhaled by the patient.

Figure 3B:
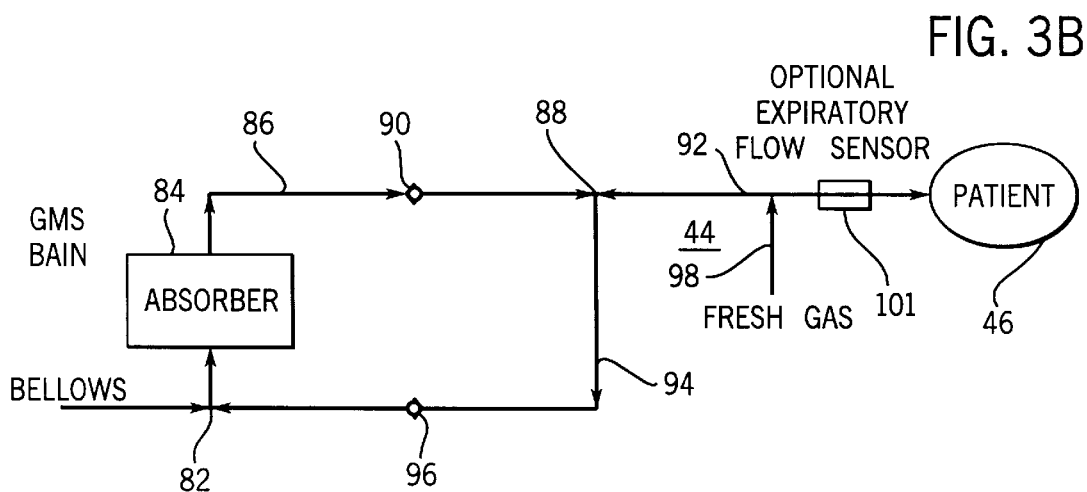

Again, with this type circuit, as shown in FIG. 3B, an optional flow sensor 101 can be located adjacent to the patient and between the fresh gas inlet 98 and the patient 46, thus the optional flow sensor 101 will also measure that additional flow provided by the fresh gas that enters the system at the fresh gas inlet 98 and which is inhaled by the patient 46 as well as measure the normal exhalation.

Figure 2C:
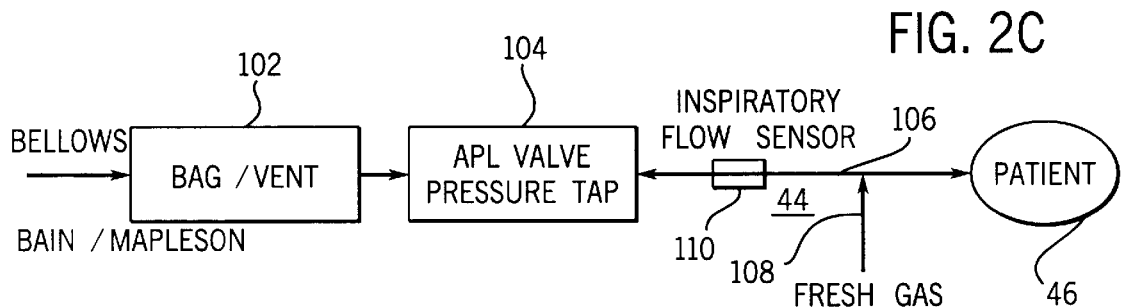

Finally, turning to FIG. 2C, there is shown a schematic view of a third representative patient breathing circuit 44, commonly known as a Bain/Mapleson circuit and which can also be used with the present invention. In that patient breathing circuit 44, the gasses from the bellows 42 flow through a bag to ventilator switch 102 and then through a pressure limiting valve 104 having a predetermined pressure limit where the valve opens to vent. The disposable patient breathing circuit 44 then comprises the main limb 106 that connects the pressure limiting valve 104 to the patient 46. Fresh gas enters the main limb 106 at fresh gas inlet 108. A flow sensor 110 is provided in the main limb 106 and again, similar to the previous Bain patient breathing circuit 44, the flow sensor 110 senses the flow delivered to the patient breathing circuit 44 from the bellows 42 during the patient's inspiration and the flow during the patient's expiration. Again the flow sensed by the flow sensor 110 will not account for that additional flow introduced into the main limb 106 at the fresh gas inlet 108 and thus will measure less that the actual flow inhaled by the patient 46. Signals representative of those flows are integrated in the processor 50, as in the previous patient breathing circuit 44, to produce signals representative of the volume delivered to the patient breathing circuit 44 from the bellows 42 to the patient 46 and the volume exhaled by the patient 46.

Figure 3C:
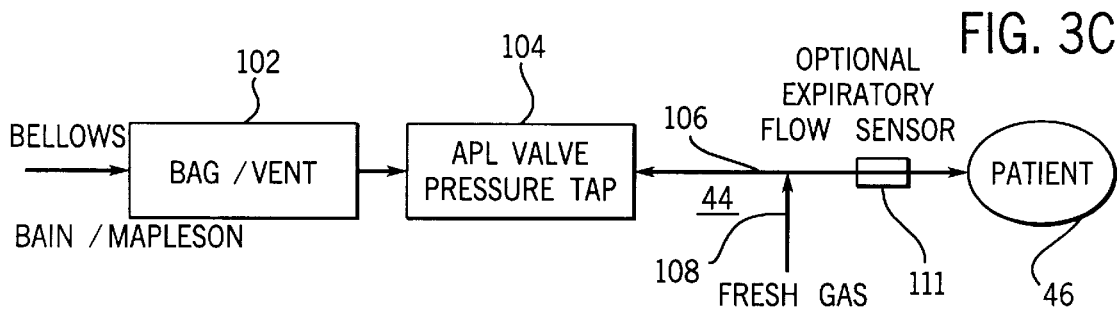

With this patient breathing circuit 44, as shown in FIG. 3C it is also possible to use an optional flow sensor 111 and which is located between the fresh gas inlet 108 and the patient 46 so that it will measure the flow from the ventilator 10 along with the additional flow of fresh gas introduced into the main limb 106 at the fresh gas inlet 108 as well as the normal exhalation.

Returning now to FIG. 1, the processor 50 uses the signals indicative of the volume of gas introduced to the patient and the volume of gas exhaled by the patient to determine an apnea condition and then, when that condition is recognized, to activate an alarm 112 to notify the clinician. In known manner, the volume signals may be digitized and displayed in conventional means so that the user can view the various volumes representative of tidal volume administered to the patient and the exhaled volumes. Prior art apnea detection means use a minimum amount of volume seen during the exhalation phase of the breath as a criteria for actuating the alarm.

In the current invention, the processor 50 includes a means to compare the values of those volumes to determine their relationship or percentage with respect to each other. Since the present invention can be used with various patient breathing circuits, there may also be an input to the processor 50 to identify to that processor 50 the actual patient breathing circuit being utilized so that the processor 50 can use the correct predetermined percentages in comparing the flows from the patient and the flow toward the patient. That input may be by means of a conventional device, such as a keyboard 114, or some keying or other identifying device may be used on the circuit itself that automatically identifies that particular patient breathing circuit to the processor 50 without intervention of the user. An example of such automatic identification includes a keying system or may even provide an electronic identification such as a EPROM to signal the processor 50 as to the particular patient breathing circuit being used. Additional processing of the volume information by processor 50 can also determine if the identification or flow sensor placement has been made incorrectly.

Processor 50 includes a timer that is started when the apnea condition is met and continues a time count. Once the count reaches a predetermined time, for example, thirty seconds, the apnea alarm 112 will be triggered.

The time count can be reset by the occurrence of a breath that does not meet the predetermined apnea criteria, thus preventing the alarm from being actuated. Similarly, the alarm, once activated, can be cleared by a breath or breaths failing to meet the apnea criteria.

Specifically, in the event the standard circle system is used as shown in FIG. 2A, having an inspiratory limb 66 and an expiratory limb 70, the exhalation volume sensed by the flow sensor 80 in the expiratory limb 70 must be at least 50 percent of the inhalation volume detected by flow sensor 78 n the inspiratory limb 66. If the processor 50 does not see that predetermined minimum percentage of volume for thirty seconds, the apnea alarm 112 will activate to alert the clinician to the apnea condition.

In that same circuit, when the optional flow sensor 81 is located between the wye piece 68 and the patient 46, that is, the optional flow sensor 81 sees both the inspired and expired gasses of the patient, the optional flow sensor 81 must see 65 percent of the volume of gas inhaled by the patient appear as exhaled volume within the thirty second period, or the apnea alarm 112 will be activated.

In the Bain circuit of FIG. 2B, where the flow sensor 100 is used for the apnea alarm, and, as explained, does not take into account the fresh gas entering the flow limb 92 through fresh gas inlet 98, therefore the processor 50 must see 100 percent of the inhaled volume detected by flow sensor 100 appear as exhaled volume detected by that same sensor 100 within the predetermined time or the processor 50 will provide a signal to activate the apnea alarm 112. In the event the optional expiratory flow sensor 101 is used in the Bain circuit and which takes into account the fresh gas entering via the fresh gas inlet 98, the criteria is that 65 percent of the volume through the optional flow sensor 101 must be seen coming back through the same sensor or an apnea condition is determined and the apnea alarm 112 activated.

With the Bain/Mapleson circuit of FIG. 2C, again a 100 percent figure is used, that is, within the predetermined period of time, the sensor 110 must see an exhalation volume equalling the volume that the same sensor detected as delivered to the patient circuit 44 in order to prevent activating the apnea alarm 112. In this same circuit, where the optional flow sensor 111 is used and which is located between the fresh gas inlet 108 and the patient 46 and thus does detect that additional fresh gas delivered to the patient, the criteria is that 65 percent of the volume inhaled by the patient and sensed by the optional flow sensor 108 must be seen as expiratory volume within the predetermined period of time or the apnea alarm 112 will be activated.

Accordingly, the present system uses both the volume delivered to the patient circuit from the bellows 42 and also the expired volume from the patient and compares the two volumes within a predetermined period of time to determine whether or not to activate the apnea alarm 112. If the volume exhaled by the patient 46 is not equal to or exceed a predetermined percentage of the delivered volume, depending on the particular circuit, the processor will activate an apnea alarm.

As noted, the description herein has been, for convenience, used with a ventilator having a bellows, however, the same apnea monitoring system can obviously be used where the ventilator does not employ a bellows but provides the gas directly to the patient breathing circuit. In addition, the apnea alarm system can be employed where the clinician is manually bagging the patient or the patient is carrying out spontaneous ventilation, the principle being that the volumes to and from the patient are sensed in order to determine the apnea condition.

While the present invention has been set forth in terms of a specific embodiment, it will be understood that the apnea detection means herein disclosed may be modified or altered by those skilled in the art to other configurations. Accordingly, the invention is to be broadly construed and limited only by the scope and spirit of the claims appended hereto.

We claim:

1. A system for determining a loss of pneumatic integrity in a medical ventilator system providing a breathing gas to a patient and receiving exhaled gas from that patient, said system comprising a ventilator providing regular breaths to the patient at predetermined timed intervals, a patient breathing circuit connected to said ventilator and for connection to the patient for communicating gas therebetween, sensor means to detect the volume of gas delivered through said patient breathing circuit to ventilate the patient and to detect the volume of gas exhaled by the patient, means to compare the volume of gas delivered to the patient through said patient circuit and the volume of gas exhaled by the patient detected by said sensor means and to provide a signal when the volume of gas exhaled by the patient is less than a predetermined percentage of the volume of gas delivered to the patient through said patient breathing circuit, and an alarm activated by said signal to alert the attending personnel of an apnea condition.

2. A system as defined in claim 1 wherein said breathing circuit is a standard circle system having an inspiratory limb and an expiratory limb, and said sensor means comprises a first sensor detecting the volume of gas passing through said inspiratory limb and a second sensor detecting the volume of gas passing through said expiratory limb.

3. A system as defined in claim 2 wherein said predetermined percentage is about 50 percent.

4. A system as defined in claim 1 wherein said breathing circuit is a standard circle system having an inspiratory limb and an expiratory limb and a wye piece for connection to the patient and said sensor means comprises a sensor located in said patient breathing circuit between said wye piece and the patient for detecting the volume of gas passing to and received from the patient.

5. A system as defined in claim 4 wherein said predetermined percentage is about 65 percent.

6. A system as defined in claim 1 wherein said patient breathing circuit comprises a flow limb for communicating the volume of gas to the patient and for receiving a volume of gas exhaled from the patient, said flow limb further having a fresh gas inlet for introducing a flow of fresh gas into the gas communicated to the patient, and wherein said sensor means is located intermediate said ventilator and said fresh gas inlet and detects the volume of gas provided from said ventilator to the patient and the volume of gas exhaled by the patient.

7. A system as defined in claim 6 wherein said predetermined percentage is about 85 percent.

8. A system as defined in claim 1 wherein said patient breathing circuit comprises a flow limb for communicating the volume of gas to the patient and for receiving a volume of gas exhaled from the patient, said flow limb further having a fresh gas inlet for introducing a flow of fresh gas into the gas communicated to the patient, and wherein said sensor means is located intermediate said fresh gas inlet and the patient and detects the volume of gas provided to the patient and the volume of gas exhaled by the patient.

9. A system as defined in claim 8 wherein said predetermined percentage is about 65 percent.

10. A system for determining an apnea condition in a medical ventilator system providing a breathing gas to a patient and receiving exhaled gas from that patient, said system comprising a ventilator, a patient breathing circuit connected to said ventilator and for connection to the patient for communicating gas therebetween, sensor means to detect the volume of gas delivered through said patient breathing circuit to the patient and to detect the volume of gas exhaled by the patient, processor means to compare the volume of gas delivered to the patient through said patient circuit and the volume of gas exhaled by the patient detected by said sensor means, means to identify the specific patient breathing circuit communicating the gas from said ventilator to the patient and to input the identification to said processor means, said processor means determining a percentage of the volume of gas exhaled by the patient with respect to the volume of gas delivered to the patient based upon said input of the specific patient breathing circuit, said processor means to comparing said volume of gas detected by said sensor means of gas exhaled by the patient with the volume of gas delivered to the patient through said patient breathing circuit, and provide a signal when said exhaled volume does not exceed said determined percentage of gas provided to the patient within a predetermined period of time, and an alarm activated by said signal to alert the attending personnel of an apnea condition.

11. A system as defined in claim 10 wherein said means to identify said specific patient breathing circuit comprises an input device manually operated by a user.

12. A system as defined in claim 10 wherein said means to identify said specific patient breathing circuit comprises a coding device in said patient breathing circuit that communicates that identification directly to said processor.

13. A system for determining a loss of pneumatic integrity in a medical gas delivery system providing a breathing gas to a patient to breath the patient at regular predetermined timed intervals and receiving exhaled gas from that patient, said system comprising a source of breathing gas, a patient breathing circuit connected to said source of breathing gas and to the patient for communicating gas therebetween, sensor means to detect the volume of gas delivered through said patient breathing circuit to ventilate the patient, at least a portion of which is from said source, and to detect the volume of gas exhaled by the patient, means to compare the volume of gas delivered to the patient through said patient circuit and the volume of gas exhaled by the patient detected by said sensor means and to provide a signal when the volume of gas exhaled by the patient is less than a predetermined percentage of the volume of gas delivered to the patient through said patient breathing circuit, and an alarm activated by said signal to alert the attending personnel of an apnea condition.

14. A system as defined in claim 13 wherein said breathing circuit is a standard circle system having an inspiratory limb and an expiratory limb, and said sensor means comprises a first sensor detecting the volume of gas passing through said inspiratory limb and a second sensor detecting the volume of gas passing through said expiratory limb.

15. A system as defined in claim 13 wherein said breathing circuit is a standard circle system having an inspiratory limb and an expiratory limb and a wye piece for connection to the patient and said sensor means comprises a sensor located in said patient breathing circuit between said wye piece and the patient detecting the volume of gas passing to and received from the patient.

16. A system as defined in claim 13 wherein said patient breathing circuit comprises a flow limb for communicating the volume of gas to the patient and for receiving a volume of gas exhaled from the patient, said flow limb further having a fresh gas inlet for introducing a flow of fresh gas into the gas communicated to the patient, and wherein said sensor means is located intermediate said source of breathing gas and said fresh gas inlet and detects the volume of gas provided from said source of breathing gas to the patient and the volume of gas exhaled by the patient.

17. A system as defined in claim 13 wherein said patient breathing circuit comprises a flow limb for communicating the volume of gas to the patient and for receiving a volume of gas exhaled from the patient, said flow limb further having a fresh gas inlet for introducing a flow of fresh gas into the gas communicated to the patient, and wherein said sensor means is located intermediate said fresh gas inlet and the patient and detects the volume of gas provided to the patient and the volume of gas exhaled by the patient.

* * * * *